(12) United States Patent
Kennedy et al.

(10) Patent No.: US 10,973,530 B2
(45) Date of Patent: Apr. 13, 2021

(54) INTRAOPERATIVELY ADJUSTING GUIDE ALIGNMENT

(71) Applicant: Smith & Nephew, Inc., Memphis, TN (US)

(72) Inventors: Eric S. Kennedy, Memphis, TN (US); Zachary C. Wilkinson, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 177 days.

(21) Appl. No.: 16/236,999

(22) Filed: Dec. 31, 2018

(65) Prior Publication Data

US 2019/0133608 A1    May 9, 2019

Related U.S. Application Data

(62) Division of application No. 14/420,437, filed as application No. PCT/US2013/054280 on Aug. 9, 2013, now Pat. No. 10,188,402.

(60) Provisional application No. 61/681,487, filed on Aug. 9, 2012.

(51) Int. Cl.
| | |
|---|---|
| *A61B 17/58* | (2006.01) |
| *A61B 17/60* | (2006.01) |
| *A61F 2/00* | (2006.01) |
| *A61B 17/15* | (2006.01) |
| *A61B 17/17* | (2006.01) |
| *A61B 17/56* | (2006.01) |

(52) U.S. Cl.
CPC ........ *A61B 17/157* (2013.01); *A61B 17/1764* (2013.01); *A61B 2017/568* (2013.01); *F04C 2270/041* (2013.01)

(58) Field of Classification Search
None
See application file for complete search history.

(56) References Cited

U.S. PATENT DOCUMENTS 5,408,409 A    4/1995    Glassman et al.
6,205,411 B1    3/2001    DiGioia, III et al.
(Continued)

FOREIGN PATENT DOCUMENTS

AU    2013299494 A1    2/2015
EP        2882375 A1    6/2015
(Continued)

OTHER PUBLICATIONS

Chao et al. "Simulation and Animation of Musculosketal Joint System" (Nov. 1, 1993) J. Biomechanical Engineering 115(4B): 562-568.
(Continued)

*Primary Examiner* — Sameh R Boles
(74) *Attorney, Agent, or Firm* — Troutman Pepper Hamilton Sanders LLP

(57) ABSTRACT

An alignment guide includes a main body sized and shaped to contact the proximal end of a tibia, and a retaining guide coupled to the main body. The retaining guide includes guide surfaces and is adjustable relative to the main body such that an operator can intra-operatively adjust the position of the guide surfaces relative to the main body to capture the anterior and posterior cruciate ligament between the guide surfaces.

11 Claims, 5 Drawing Sheets

(56) References Cited

U.S. PATENT DOCUMENTS

| | | | |
|---|---|---|---|
| 8,974,459 B1* | 3/2015 | Axelson, Jr. | A61B 17/154 606/86 R |
| 2010/0305575 A1* | 12/2010 | Wilkinson | A61B 17/155 606/88 |
| 2011/0060341 A1 | 3/2011 | Angibaud et al. | |
| 2012/0179266 A1 | 7/2012 | Collazo | |

FOREIGN PATENT DOCUMENTS

| | | |
|---|---|---|
| WO | 2012051542 A2 | 4/2012 |
| WO | 2014026084 A1 | 2/2014 |

OTHER PUBLICATIONS

Chiu et al., 'Review article: knee flexion after total knee arthroplasty' Journal of Orthopaedic Surgery, vol. 10, No. 2, pp. 194-202 (2002).

Delp et al. "An Interactive Graphics-Based Model of the Lower Extremity to Study Orthopaedic Surgical Procedures" (Aug. 1990) IEE Transactions on Biomedical Engineering 37(8): 757-767.

DiGioia et al. "An Integrated Approach to Medical Robotics and Computer Assisted Surgery in Orthopaedics" (1995) Carnegie Mellon University 106-111.

DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.

Dillman et al. "Haptic Devices in Medical Applications" (Jun. 23, 1999) Institute for Process Control and Robotics, 1st International Workshop, Paris, France, pp. 12-22.

Freysinger et al. "A Passive-Marker-Based Optical System for Computer-Aided Surgery in Otorhinolaryngology: Development and First Clinical Experiences" (Feb. 2002) The Laryngoscope 112(2):409.

Harris et al. "Experiences with Robotic Systems for Knee Surgery" (Mar. 19-22, 1997) Springer-Verlag, London, UK 757-766.

International Search Report for PCT/US2013054280 dated Oct. 22, 2013.

O'Toole III et al. "Towards More Capable and Less Invasive Robotic Surgery in Orthopaedics" (1995) Computer Vision, Virtual Reality and Robotics in Medicine 905: 123-130.

Ong et al., 'Total knee arthroplasty using a hybrid navigation technique' Journal of Orthopaedic Surgery and Research, vol. 6, Article No. 26, internal pp. 1-6 (2010).

Smith & Nephew Inc., 'Legion porous CR: cruciate retaining femoral' Catalog, pp. I-13 (2009).

Taylor et al. "An Image-Directed Robotic System for Precise Orthopaedic Surgery" (Jun. 1994) IEE Transactions on Robotics and Automation 10 (3): 261-275.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

Written Opinion for PCT/US2013054280 dated Oct. 22, 2013.

Zimmer Inc., 'Cruciate retaining (CR) and revision instrumentation surgical technique for cruciate retaining augment able (CRA) knees' Catalog, pp. I-138 (2011) See pp. 49-53 and figures 73-89.

European Search Report for counterpart European Application No. 13827135.8, dated Feb. 5, 2016.

Australian Examination Report No. 1 for counterpart Australian Patent Application No. 2013299494, dated Feb. 16, 2017.

* cited by examiner

INTRAOPERATIVELY ADJUSTING GUIDE ALIGNMENT

CROSS-REFERENCE TO RELATED APPLICATIONS

This application is a divisional application of U.S. patent application Ser. No. 14/420,437, filed Feb. 9, 2015, and titled "Intraoperatively adjusting guide alignment," which is a U.S. national stage filing under 35 U.S.C. § 371 of PCT Application No. PCT/US2013/054280, filed Aug. 9, 2013, and titled "Intraoperatively adjusting guide alignment," which claims priority to and the full benefit of U.S. Provisional Application Ser. No. 61/681,487, filed Aug. 9, 2012, and titled "INTRAOPERATIVELY ADJUSTING GUIDE ALIGNMENT," the entire contents of each of which are incorporated herein by reference.

BACKGROUND

Cutting guides are used during orthopaedic procedures to insert pins in hone and guide resections to the bone to prepare the bone for receipt of an implant. For example, during bi-cruciate retaining total knee arthroplasty, a cutting guide used to prepare the proximal end of a patient's tibia is designed the leave intact portions of the tibial eminence that function as attachment sites for the anterior and posterior cruciate ligaments.

SUMMARY

A cutting guide for preparing the proximal end of a patient's tibia is described in International Application WO 2012/051542, titled Patient-Matched Instrumentation and Methods, hereby incorporated by reference in its entirety. Prior to placing the cutting guide on the bone, an alignment guide can be used to preposition alignment pins over which the cutting guide is subsequently placed to guide bone resections.

An alignment guide can include a ligament retaining guide that is adjustably mounted to a main body of the cutting guide to allow the operator to intra-operatively adjust the position of the retaining guide. Adjusting the retaining guide aligns, for example, pin receiving holes of the retaining guide through which the alignment pins are placed in the bone.

In a particular example, the alignment guide is configured to mount to the proximal end of a patient's tibia. The alignment guide has a bone mount, for example, a portion of the alignment guide that defines the pin receiving holes, and a pair of horizontal rods spaced to capture the anterior and posterior cruciate ligaments therebetween that are used to visualize subsequent eminence resections.

According to one aspect, an alignment guide includes a main body sized and shaped to contact the proximal end of a tibia, and a retaining guide coupled to the main body. The retaining guide includes guide surfaces and is adjustable relative to the main body such that an operator can intra-operatively adjust the position of the guide surfaces relative to the main body to capture the anterior and posterior cruciate ligament between the guide surfaces.

Embodiments of this aspect may include one or more of the following features.

The retaining guide is coupled to the main body such that the position of the retaining guide is rotationally and linearly adjustable relative to the main body. The retaining guide includes a bone mount that defines through holes. The main body includes a horseshoe shaped upper portion having surfaces for contacting the proximal surface of the tibia, and a lower portion having surfaces for contacting the anterior face of the proximal end of the tibia. The bone contacting surfaces of the main body comprise patient-matched surfaces. The main body defines a slot.

The main body defines a through hole that receives the retaining guide, and the retaining guide includes a shaft received in the through hole with the shaft being rotatable relative to the main body. The retaining guide includes a bone mount coupled to the shaft for linear motion relative to the shaft.

According to another aspect, a method includes positioning an alignment guide on the proximal tibia, the alignment guide including a main body and a retaining guide; and intra-operatively adjusting the position of the retaining guide relative to the main body to capture the anterior and posterior cruciate ligament.

The details of one or more embodiments are set forth in the accompanying drawings and the description below. Other features, objects, and advantages will be apparent from the description and drawings, and from the claims.

DETAILED DESCRIPTION

Figure 1:
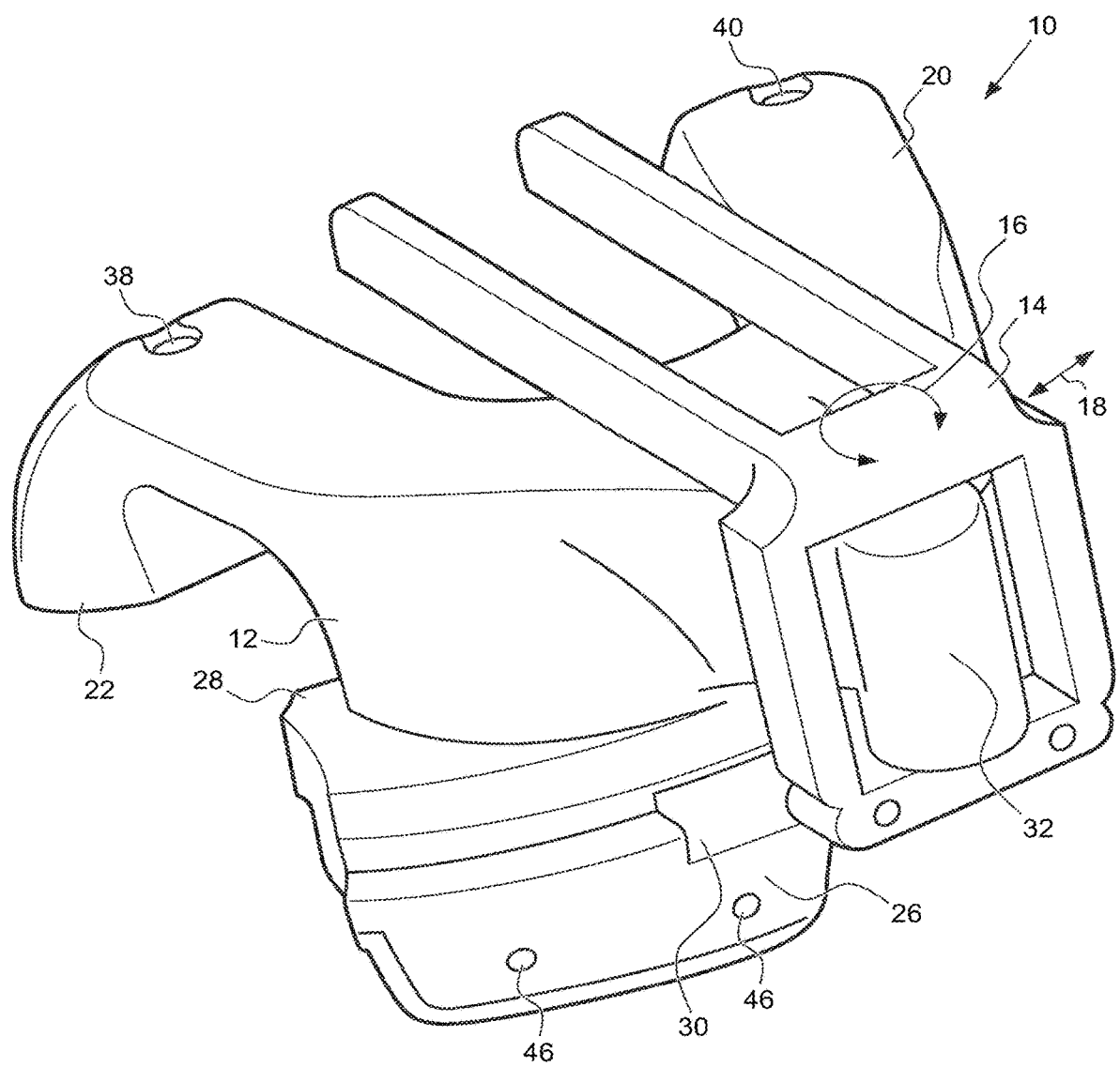
FIG. 1 is a perspective view of an alignment guide.

Referring to FIG. 1, an alignment guide 10 for placing pins for use in aligning a cutting guide that prepares a proximal tibia for receipt of an implant during bi-cruciate retaining total knee arthroplasty includes a main body 12 and a cruciate retaining guide 14. The retaining guide 14 can rotate, arrow 16, and translate, arrow 18, relative to the main body 12 to provide intraoperative adjustability of the position of the retaining guide 14 relative to the main body 12.

Figure 2:
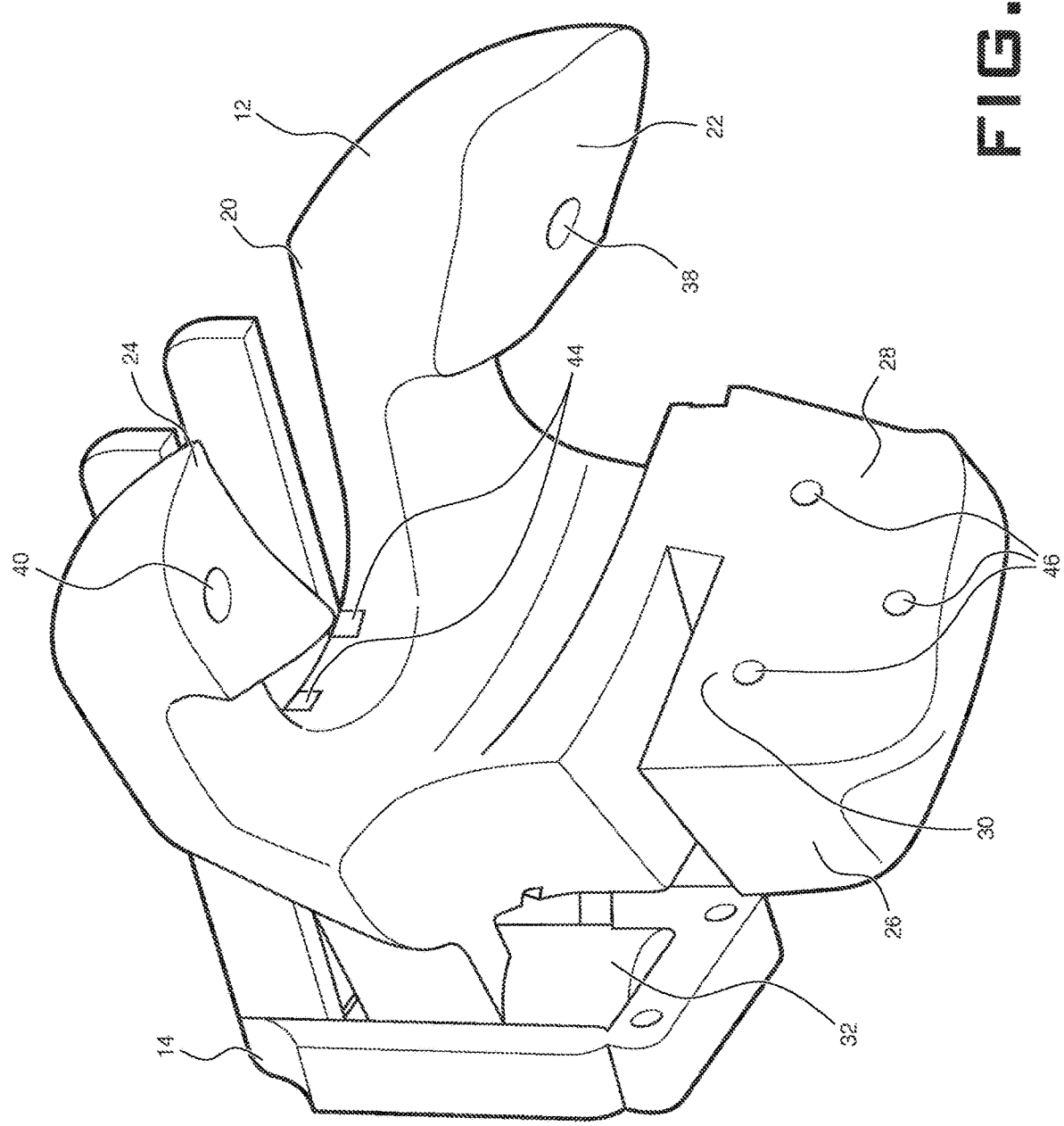
FIG. 2 is another perspective view of the alignment guide.

Referring also to FIG. 2, the main body 12 includes a horseshoe shaped upper portion 20 having surfaces 22, 24 for contacting the proximal surface of the tibia, and a lower portion 26 having a medial surface 28 for contacting the anterior face of the proximal end of the tibia. The bone contacting surfaces 22, 24, 28 of the main body are, for example, patient-matched surfaces. The lower portion 26 can also include a lateral surface or have a lateral surface rather than the medial surface 28.

Figure 3:
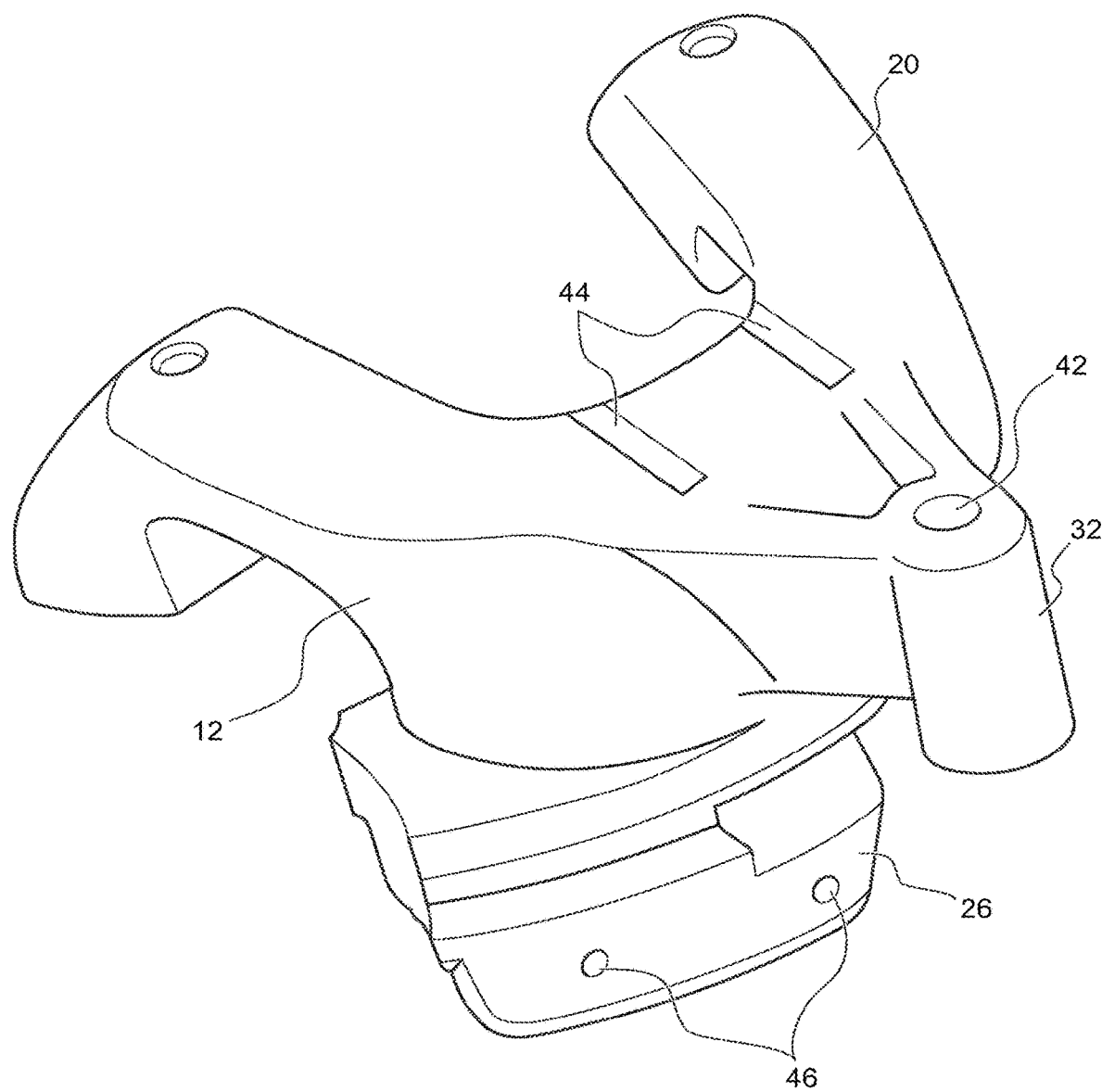
FIG. 3 is a perspective view of a main body of the alignment guide.

The lower portion 26 defines a slot 30 through which alignment pins (not shown) are placed into the bone. The upper portion 20 defines through holes 38, 40 and the lower portion 26 defines through holes 46 for receiving fixation pins (not shown) used to fix the main body 12 to the tibia. On the anterior side of the upper portion 20 is a retaining guide mount 32 defining a through hole 42 (FIG. 3) that receives the retaining guide 14. The superior side of the upper portion 20 defines two slots 44 that function as indicia to aid in aligning the retaining guide 14 relative to the main body 12.

Figure 4:
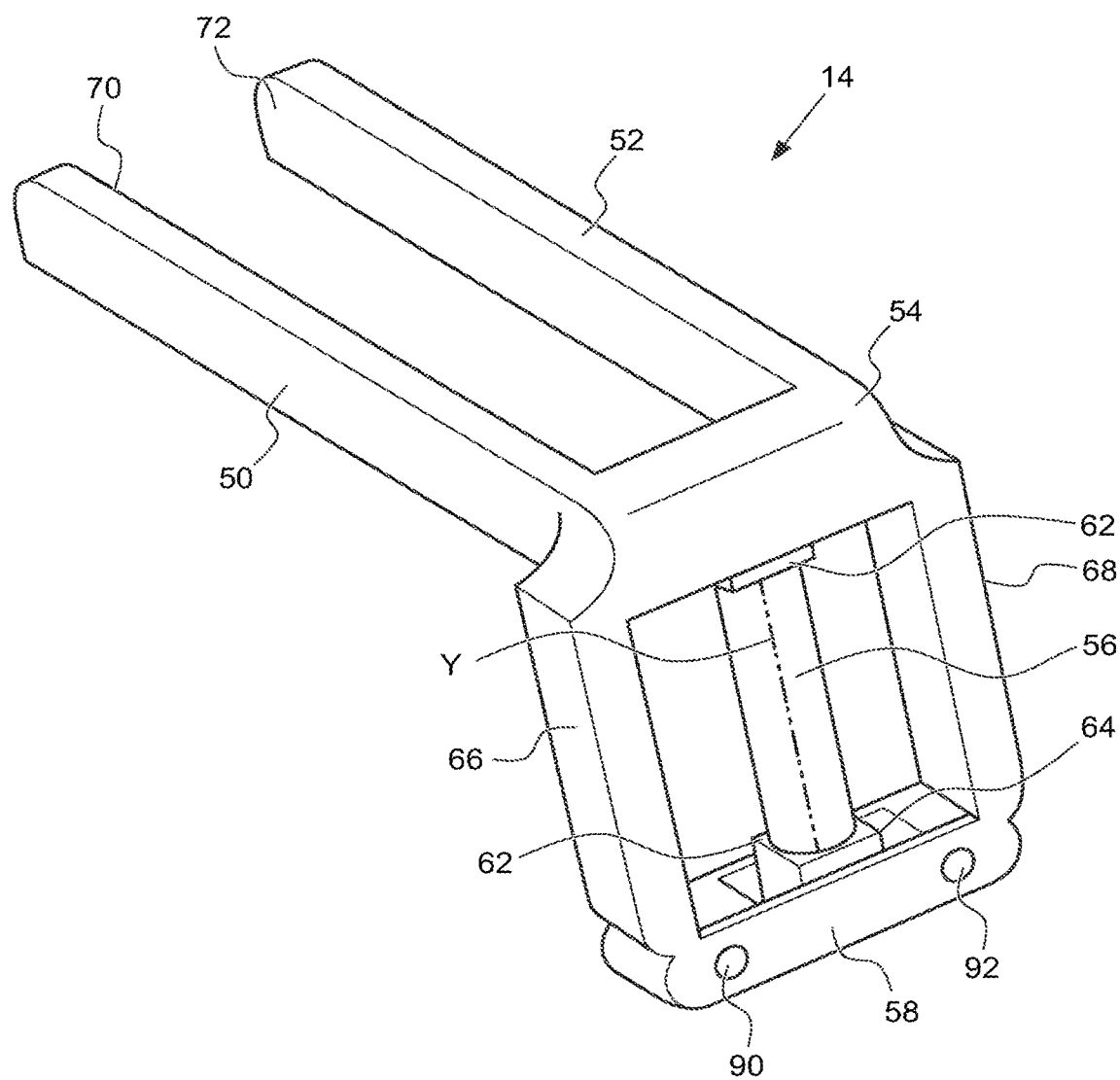
FIG. 4 is a perspective view of a cruciate retaining guide of the alignment guide.

Referring to FIG. 4, the retaining guide 14 includes two horizontal rods 50, 52 connected by a cross bar 54, a bone mount 58 connected to the cross bar 54 by two vertical bars 66, 68, and a shaft 56 that extends between the cross bar 54 and the bone mount 58. At each end the shaft 56 terminates in a rectangular block 62. One of the blocks 62 is received within a slot 64 defined by bone mount 58 and the other block 62 is received within a corresponding slot (not shown) defined by the cross bar 54. The blocks 62 can slide within the slots 64 to provide the translation along arrow 18. The shaft 56 can rotate about its longitudinal axis, Y, within the through hole 42 of the retaining guide mount 32.

The retaining guide rods 50, 52 each have inner guide surfaces 70, 72, respectively, used to visualize the alignment of subsequent eminence resections. The retaining guide 14 is coupled to the main body 12 via through hole 42 and shaft 56 such that in use the guide rods 50, 52 are positioned to capture the cruciate ligaments therebetween. By aligning the guide rods 50, 52 with the indicia slots 44, the operator positions the retaining guide 14 to achieve best fit and coverage of a presumed implant. The operator can deviate from this alignment by adjusting the position of the retaining guide 14. The operator may decide to deviate from alignment with the indicia slots 44 for the sake of aligning the eminence resections with the femur or a femoral trial in extension and/or flexion. To allow the patient's leg to be placed in extension with the alignment guide 10 on the tibia, medial and lateral sections of the upper portion 20 of the main body 12 are made excisable from the remainder of the main body by, for example, including perforations or webs in the upper portion.

Figure 5:
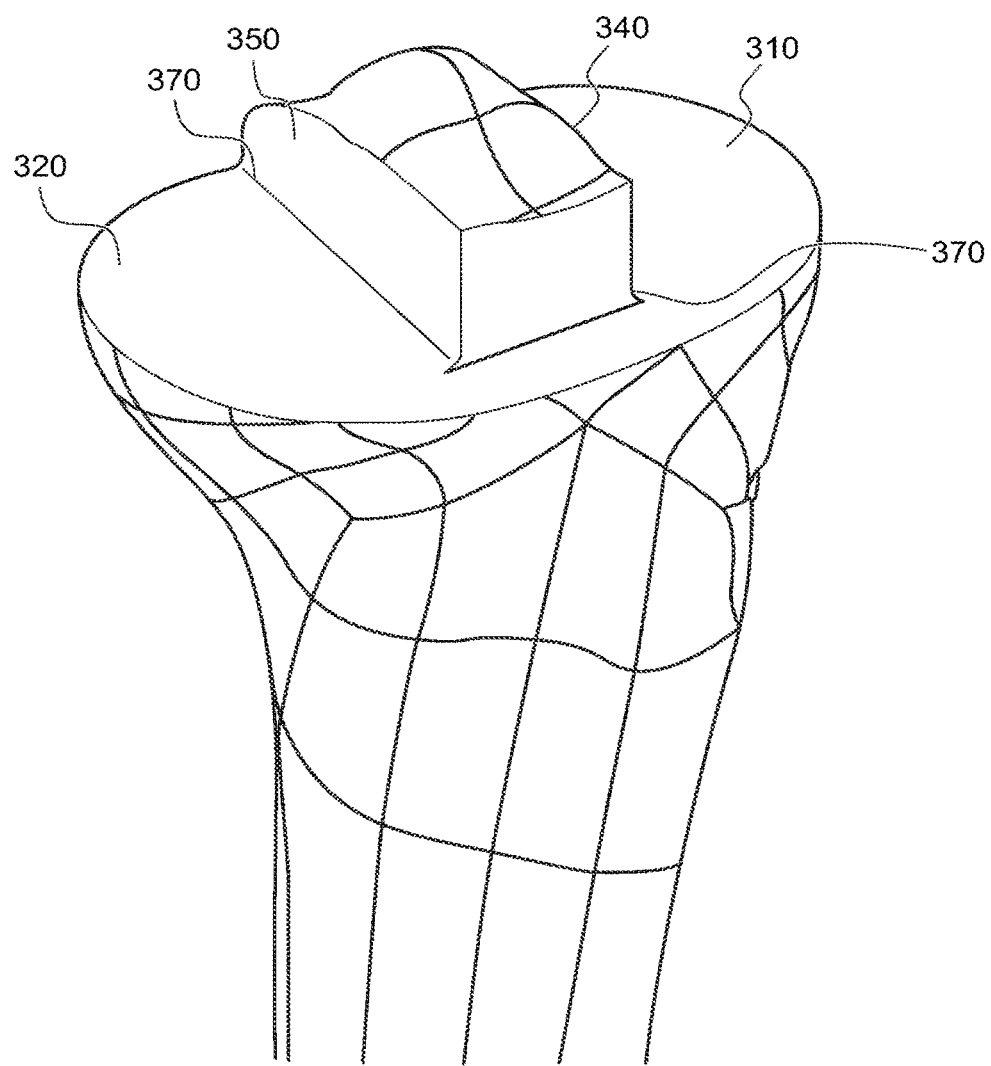
FIG. 5 illustrates a tibia after plateau and eminence resections have been made.

The bone mount 58 defines two through holes 90, 92, each for receiving an alignment pin. The relative position of the holes 90, 92 and the guide surfaces 70, 72 correspond to the relative position of pin receiving holes and cutting guide surfaces on a cutting block, for example, a patient matched cutting block. Referring also to FIG. 5, due to the corresponding relative positions, when the alignment pins placed through holes 90, 92 are subsequently used to place the cutting block, the alignment pins are positioned at the intersection of subsequent horizontal plateau resections 310, 320 and vertical eminence resections 340, 350 made using the cutting guide, creating curved sections 370 at the intersections.

In use, after the main body 12 is fixed to the proximal end of the tibia using pins placed through holes 38, 40, and 46, the operator intra-operatively adjusts the position of the retaining guide 14 relative to the main body 12 about arrow 16 and along arrow 18 to adjust the position of the guide surfaces 70, 72 relative to the main body 12. Fixing the main body 12 to the tibia fixes three degrees of freedom of movement of the retaining guide 14. Rotation about arrow 16 and sliding along arrow 18 permits adjustment of an additional two degrees of freedom of movement of the retaining guide 14.

When the operator determines that the guide surfaces 70, 72, and thus the resulting vertical eminence resections 340, 350, are adequately spaced from the attachment sites of the cruciate ligaments, the operator places the alignment pins through holes 90, 92. The operator then removes the alignment guide 10 leaving the alignment pins in place in the bone, and places a cutting block over the alignment pins. The cutting block can include patient-matched bone contacting surfaces that correspond to bone contacting surfaces 22, 24, 28 of the main body 12. The discrete bone contacting surfaces allow some adjustability in the placement of the patient-matched cutting block to allow the cutting block to be aligned with the alignment pins.

The main body of a patient-matched alignment guide can be created from a MRI scan and X-rays, or other imaging modalities such as CT. The main body can be made of nylon on a rapid prototyping machine or other plastics, ceramics, or metals can be used. The main body can be machined. The main body can have a different geometry and touch different parts of the anatomy. The retaining guide is made, for example, from metal and can be reusable or disposable.

Other embodiments are within the scope of the following claims.

For example, the retaining guide can be locked in a desired position. Continuous planar adjustment between the main body and the retaining guide (combined medial-lateral and internal-external) can be provided by a planar joint that has plane-to-plane contact rather than a sliding/rotating joint. The retaining guide can be configured to be moved inferior-superior in addition to medial-lateral and internal-external to enable the retaining guide to be moved closer to the eminence. Alternatively, part of the upper portion of the main body can be removable once the alignment guide 10 is pinned to the tibia so that the retaining guide has room to drop down closer to the eminence.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method comprising:
   positioning an alignment guide on a proximal tibia, the alignment guide including a main body defining a through hole and a retaining guide,
   wherein the main body includes an upper portion having surfaces for contacting the surface of the proximal tibia, and a lower portion having surfaces for contacting the anterior face of the proximal tibia,
   wherein the retaining guide comprises guide surfaces, a shaft rotatable relative to the main body, and a bone mount coupled to the shaft for linear motion relative to the shaft, wherein the retaining guide is coupled to and rotationally and linearly adjustable relative to the main body, and
   wherein the through hole receives the shaft; and
   intraoperatively adjusting the position of the retaining guide relative to the main body to capture an anterior cruciate ligament and a posterior cruciate ligament between the guide surfaces.

2. The method of claim 1, wherein the surfaces of the upper portion and the lower portion of the main body comprise patient-matched surfaces.

3. The method of claim 1, wherein the upper portion of the main body is horseshoe-shaped.

4. The method of claim 1, wherein the main body further defines a slot for aligning the retaining guide relative to the main body.

5. A method comprising:
- positioning an alignment guide on a proximal tibia, the alignment guide including a main body and a retaining guide; and
- intraoperatively adjusting the position of the retaining guide relative to the main body to capture an anterior cruciate ligament and a posterior cruciate ligament,
- wherein the main body has a guide mount, a lower portion, and an upper portion,
- wherein the retaining guide includes at least one horizontal rod connected to a cross bar, a bone mount connected to the cross bar by at least one vertical bar, and a shaft extending between the cross bar and the bone mount,
- wherein each end of the shaft terminates in a sliding block, and the sliding blocks are received in slots of the cross bar and the bone mount, and
- wherein the guide mount has a through hole configured to receive the shaft of the retaining guide.

6. The method of claim 5, wherein intraoperatively adjusting the position of the retaining guide comprises adjusting the position of the retaining guide rotationally and adjusting the position of the retaining guide linearly.

7. The method of claim 6, wherein adjusting the position of the retaining guide rotationally includes rotating the retaining guide relative to the main body.

8. The method of claim 6, wherein adjusting the position of the retaining guide linearly includes sliding the retaining guide relative to the main body.

9. The method of claim 5, wherein the upper portion of the main body is horseshoe-shaped.

10. The method of claim 5, wherein the sliding blocks are rectangular.

11. A method comprising:
- positioning an alignment guide on a proximal tibia, the alignment guide including a main body and a retaining guide; and
- intraoperatively adjusting the position of the retaining guide relative to the main body to capture an anterior cruciate ligament and a posterior cruciate ligament;
- wherein the main body has a guide mount, a lower portion, and a horseshoe-shaped upper portion with a first surface and a second surface, the guide mount having a through hole;
- wherein the retaining guide includes two horizontal rods connected by a cross bar, a bone mount connected to the cross bar by two vertical bars, and a shaft extending between the cross bar and the bone mount;
- wherein each end of the shaft terminates in a rectangular block, and the rectangular blocks are received in slots of the cross bar and the bone mount; and
- wherein the through hole is configured to receive the shaft.

* * * * *